US012590048B2

United States Patent

(12) United States Patent
Maeda et al.

(10) Patent No.: US 12,590,048 B2
(45) Date of Patent: Mar. 31, 2026

(54) DINAPHTHYL ETHER COMPOUND AND LUBRICANT COMPOSITION CONTAINING SAME

(71) Applicant: MORESCO CORPORATION, Kobe (JP)

(72) Inventors: Tatsuya Maeda, Hyogo (JP); Mayumi Hayashi, Hyogo (JP); Kohei Yamashita, Hyogo (JP); Masayuki Hata, Hyogo (JP)

(73) Assignee: MORESCO CORPORATION, Kobe (JP)

(*) Notice: Subject to any disclaimer, the term of this patent is extended or adjusted under 35 U.S.C. 154(b) by 493 days.

(21) Appl. No.: 18/276,162

(22) PCT Filed: Feb. 9, 2022

(86) PCT No.: PCT/JP2022/005004

§ 371 (c)(1),
(2) Date: Aug. 7, 2023

(87) PCT Pub. No.: WO2022/172935

PCT Pub. Date: Aug. 18, 2022

(65) Prior Publication Data

US 2024/0116841 A1 Apr. 11, 2024

(30) Foreign Application Priority Data

Feb. 12, 2021 (JP) ................................ 2021-020368

(51) Int. Cl.
*C07C 43/275* (2006.01)
*C10M 129/16* (2006.01)
*C10M 169/04* (2006.01)
*C10N 30/08* (2006.01)

(52) U.S. Cl.
CPC ......... *C07C 43/275* (2013.01); *C10M 129/16* (2013.01); *C10M 169/04* (2013.01); *C10M 2207/04* (2013.01); *C10N 2030/08* (2013.01)

(58) Field of Classification Search
None
See application file for complete search history.

(56) References Cited

U.S. PATENT DOCUMENTS

| | | | | |
|---|---|---|---|---|
| 4,664,829 | A | 5/1987 | Arakawa et al. | |
| 4,892,680 | A * | 1/1990 | Ishida .................. | C10M 105/38 508/505 |
| 2015/0166447 | A1* | 6/2015 | Hayashi ................ | C07C 43/275 508/581 |

FOREIGN PATENT DOCUMENTS

| | | |
|---|---|---|
| JP | 62-44797 | 9/1987 |
| JP | 62-59760 | 12/1987 |

OTHER PUBLICATIONS

International Search Report issued Apr. 19, 2022 in International (PCT) Application No. PCT/JP2022/005004.

* cited by examiner

*Primary Examiner* — Medhanit W Bahta
(74) *Attorney, Agent, or Firm* — Wenderoth, Lind & Ponack, L.L.P.

(57) ABSTRACT

One aspect of the present invention relates to a dinaphthyl ether compound represented by formula (1):

[Chemical Formula 1]

(1)

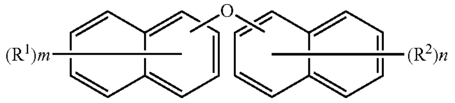

in the formula (1), $R^1$ and $R^2$ are the same or different and each represent a linear or branched hydrocarbon group having 6 to 32 carbon atoms; m and n are each a real number of 0 or more and satisfy $1.0 \leq m+n \leq 3.0$.

6 Claims, 1 Drawing Sheet

DINAPHTHYL ETHER COMPOUND AND LUBRICANT COMPOSITION CONTAINING SAME

TECHNICAL FIELD

The present invention relates to a dinaphthyl ether compound, and a lubricating oil composition and the like containing the same.

BACKGROUND ART

Lubricating oils and lubricating oil compositions are used for reducing friction and wear between moving parts or moving surfaces of various mechanical devices and the like.

In particular, lubricating oils, lubricating greases, and the like are being used under severer conditions such as high temperature, high speed, high load, and radiation, and lubricating oil agents having further improved heat resistance are required.

When the use condition becomes high in temperature and high in speed, lubricating oils, greases, and the like used for lubrication undergo temperature rise, thermal degradation, or oxidative degradation due to oil film breakage, and promotion of evaporation of lubricant base oils caused thereby leads to generation of sludge, breakage of a machine device, and life reduction.

For this reason, various lubricating oils and greases that can be used under high-temperature conditions have been studied, and in general, improvement under high-temperature conditions is largely caused by base oils contained most in the compositions of the lubricating oils and the greases.

Up to date, a phenyl ether-based synthetic lubricating oil containing, as an active ingredient, polyphenyl ether having 3 to 5 phenyl groups and at least one alkyl substituent having 10 to 20 carbon atoms has been known as a lubricating oil having heat resistance (Patent Literature 1). In addition, a radiation-resistant lubricating oil containing 0 to 70 weight % of o-(m-phenoxyphenoxy)diphenyl, 25 to 75% of m-(m-phenoxyphenoxy)diphenyl, and 75 to 25% of monoalkyldiphenyl ether or dialkyldiphenyl ether having 10 to 20 alkyl carbon atoms is known as a lubricating oil having radiation resistance (Patent Literature 2).

The lubricating oil agent described in Patent Literatures 1 and 2 is superior in heat resistance and radiation resistance, but currently, lubricating oil agents such as lubricating oil and lubricating grease have increasingly been used under severer conditions, and lubricating oil agents having further superior heat resistance are required.

CITATION LIST

Patent Literatures

Patent Literature 1: JP-B-S62-44797
Patent Literature 2: JP-B-S62-59760

SUMMARY OF INVENTION

A task of the present invention is to solve the above problems. That is, an object of the present invention is to provide a compound which has further superior heat resistance and can be used as a lubricating oil that can be used under severer conditions.

As a result of intensive studies to solve the above task, the present inventors found that the above object is achieved by a dinaphthyl ether compound having the following configuration, and achieved the present invention by further conducting studies based on that finding.

That is, the dinaphthyl ether compound according to one aspect of the present invention is a compound represented by the following formula (1):

[Chemical Formula 1]

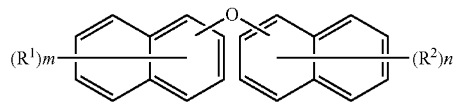
(1)

in the formula (1), $R^1$ and $R^2$ are the same or different and each represent a linear or branched hydrocarbon group having 6 to 32 carbon atoms; m and n are each a real number of 0 or more and satisfy $1.0 \leq m+n \leq 3.0$.

DESCRIPTION OF EMBODIMENTS

Figure 1:
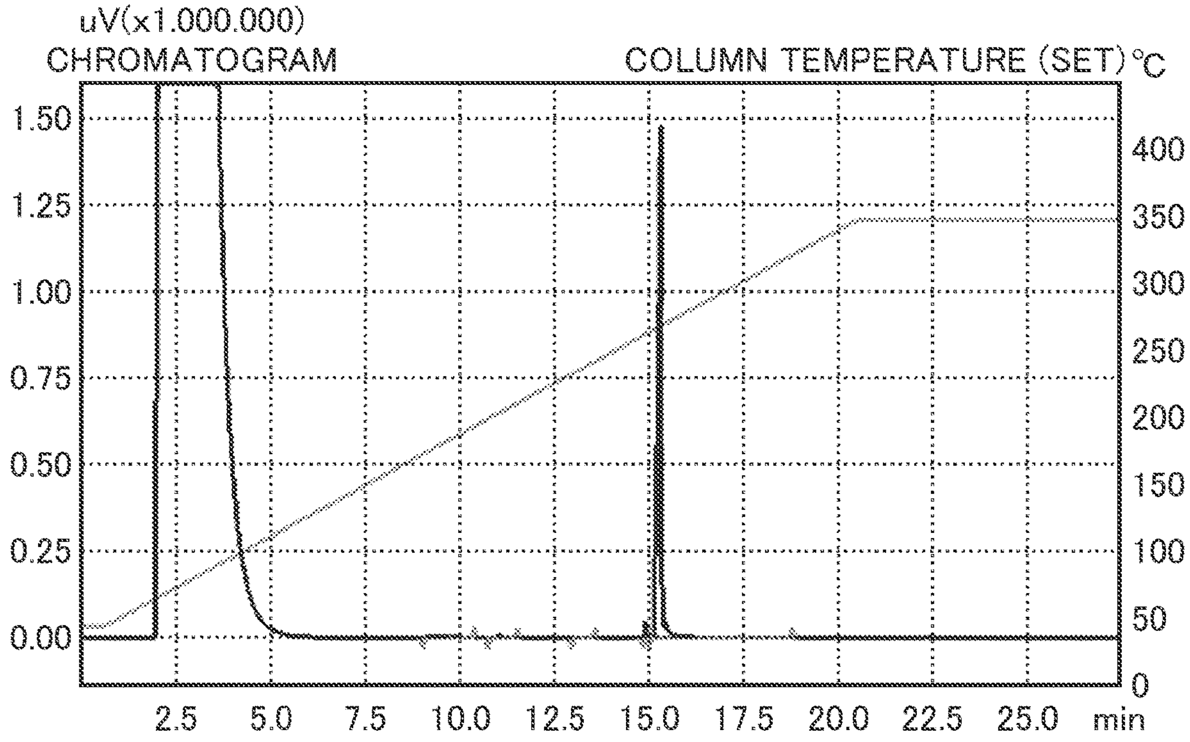
FIG. 1 shows a gas chromatography (GC) chart of the dinaphthyl ether synthesized in Example 1.

The dinaphthyl ether compound of the present invention is a compound represented by the following formula (1) as described above.

[Chemical Formula 2]

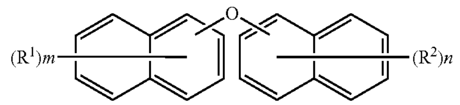
(1)

In the formula (1), $R^1$ and $R^2$ are the same or different and each represent a linear or branched hydrocarbon group having 6 to 32 carbon atoms. In addition, m and n are each a real number of 0 or more and satisfy $1.0 \leq m+n \leq 3.0$.

The dinaphthyl ether compound having such a configuration is very useful as a lubricating oil because the naphthyl phenyl ether compound has excellent heat resistance while maintaining lubricity equivalent to that of conventional compounds like those described in the above-mentioned prior art documents. More specifically, since the dinaphthyl ether compound exhibits a small evaporation loss at a high temperature and has a long life at a high temperature, the naphthyl phenyl ether compound can be suitably used as a base oil of a lubricating oil for high temperature or a heat-resistant grease to be used at higher temperatures.

Therefore, according to the present invention, it is possible to provide a dinaphthyl ether compound that has further superior heat resistance and is used as a lubricating oil capable of being used under severer conditions.

Hereinafter, an embodiment of the present invention will be described in detail, but the present invention is not limited thereto.

The dinaphthyl ether compound of the present embodiment is a compound represented by the formula (1) provided above.

In the formula (1), $R^1$ and $R^2$ are the same or different and each represent a hydrocarbon group having 6 to 32 carbon atoms, and for example, when either m or n in the formula (1) is 0, either one of $R^1$ and $R^2$ may be a hydrogen atom. In other words, although either one of $R^1$ and $R^2$ may be a hydrogen atom, at least one of $R^1$ and $R^2$ is the hydrocarbon group defined above.

When the number of carbon atoms in the hydrocarbon group is less than 6, physical properties of dinaphthyl ether, which has no hydrocarbon groups, greatly act and the dinaphthyl ether compound is prone to have poor fluidity. In addition, its small molecular weight leads to a large evaporation amount. On the other hand, it is considered that when the number of carbon atoms in the hydrocarbon group exceeds 32, the interaction between molecules increases, so that the viscosity becomes excessively high and exceeds the viscosity range commonly used. When the number of carbon atoms in the hydrocarbon group is 6 to 32, the balance between heat resistance and low-temperature characteristics is good, which is favorable. The lower limit value of the number of carbon atoms in the hydrocarbon group is more preferably 16 or more, and the upper limit value is more preferably 28 or less.

In the present embodiment, the structure of the hydrocarbon group having 6 to 32 carbon atoms is linear or branched. Specifically, examples of the linear hydrocarbon group include alkyl groups such as a hexyl group, an octyl group, a decyl group, a dodecyl group, a tetradecyl group, a hexadecyl group, an octadecyl group, an icosyl group, a docosyl group, a tetracosyl group, a hexacosyl group, and an octacosyl group; alkylene groups such as an octene group, a decene group, a hexadecene group, a dodecene group, an octadecene group, an icosene group, a dococene group, a techolacocene group, a hexacocene group, and an octacocene group; and a cyclohexyl group. Examples of the branched hydrocarbon group include a 1-methylundecyl group, a 1-ethyldecyl group, a 1-methyltridecyl group, a 1-ethyldodecyl group, a 1-methylpentadecyl group, a 1-ethyltetradodecyl group, a 1-methylheptadecyl group, a 1-ethyloctadecyl group, a 1-methylnonadecyl group, a 1-ethyloctadecyl group, a 2-ethylhexyl group, a 2-octyldodecyl group, a 2-decyltetradecyl group, a 2-dodecylhexadecyl group, a 1-butyl-1-methylpentyl group, a 1-butyl-1-methylheptyl group, a 1-methyl-1-pentyloctyl group, a 1-hexyl-1-methylnonyl group, a 1-heptyl-1-methyldecyl group, a 1-methyl-1-octylundecyl group, a 1-decyl-1-methyltridecyl group, a 1-dodecyl-1-methylpentadecyl group, a 2-octyldodecene group, a 2-decyltetradecene group, and a cyclohexyl group. The hydrocarbon group is preferably a saturated hydrocarbon group because of superior thermal stability. A plurality of kinds of the hydrocarbon group may be used at the same time. In this case, the number of carbon atoms of the hydrocarbon groups is represented by an average thereof.

Among these hydrocarbon groups, a hydrocarbon group having 12 to 32 carbon atoms is preferable from the viewpoint of affording further superior heat resistance, and preferred examples thereof include a 1-methylundecyl group, a 1-methyltridecyl group, a 1-methylpentadecyl group, a 1-methyl-1-octylundecyl group, a 1-decyl-1-methyltridecyl group, a 1-dodecyl-1-methylpentadecyl group, a hexadecyl group, a dodecyl group, a tetradecyl group, a 2-octyldodecyl group, a 2-decyltetradecyl group, and a 2-dodecylhexadecyl group.

In the formula (1), as long as m and n satisfy $1.0 \leq m+n \leq 3.0$, the hydrocarbon group as described above may be bonded to either of two naphthyl groups and may be bonded to any position of the naphthyl groups. For example, when m+n is 1, either $R^1$ or $R^2$ may be a hydrogen atom.

In the compound of the formula (1), m and n are each a real number of 0 or more, and satisfy $1.0 \leq m+n \leq 3.0$. When m+n is less than 1.0, it is considered that physical properties of dinaphthyl ether, which has no hydrocarbon groups, appear and the fluidity is deteriorated. In addition, a small molecular weight thereof makes it impossible to sufficiently control the evaporation amount. On the other hand, when m+n exceeds 3.0, this leads to a large interaction between molecules and affords an excessively high viscosity. In the present embodiment, m+n represents the number of substitution with linear or branched hydrocarbon groups (hereinafter, also simply referred to as the number of alkyl substitution).

The compound of the present embodiment may be, for example, a mixture of a compound with $0 \leq m+n \leq 2.0$ and a compound with $2.0 \leq m+n \leq 3.0$. In the case of a mixture of a plurality of compounds having different m+n values as described above, the value of m+n means the average value of m+n of the dinaphthyl ether compounds contained in the compound of the present embodiment.

In a preferred embodiment, the m+n is more desirably 1 or more and 2.5 or less.

In the present embodiment, the number of substitution with hydrocarbon groups can be measured by the method described in Examples described later.

Preferably, the mass average molecular weight of the dinaphthyl ether compound of the present embodiment is approximately 450 to 800. When the mass average molecular weight of the dinaphthyl ether compound is large, there is an advantage that the compound is superior in heat resistance. Therefore, when the mass average molecular weight is in the above range, the kinematic viscosity and the pour point are not excessively high and the compound is superior in heat resistance. On the other hand, when the mass average molecular weight is smaller than the above range, the heat resistance tends to be poor.

The mass average molecular weight of the dinaphthyl ether compound in the present embodiment is a value measured using $^1$H-NMR as shown in Examples described later. Hereinafter, the mass average molecular weight is also simply referred to as "average molecular weight".

The method for producing the dinaphthyl ether compound as described above is not particularly limited, but for example, the naphthyl phenyl ether compound can be obtained by the following synthesis method.

First, 2-naphthol and N-methyl-2-pyrrolidone (hereinafter, referred to as NMP) are mixed with potassium carbonate and copper iodide, followed by purging with nitrogen, and then 1-bromonaphthalene is added dropwise thereto to afford dinaphthyl ether.

Next, the dinaphthyl ether compound of the present embodiment can be obtained, for example, by reacting the naphthyl ether with a linear or branched olefin or the like using aluminum chloride or the like as a catalyst.

The present invention also includes a lubricating oil composition containing the dinaphthyl ether compound described above.

In addition to the dinaphthyl ether compound, a mineral oil and a synthetic oil such as an α-olefin oligomer, a polyol ester, a diester, a polyalkylene glycol, silicone oil, a modified silicone oil, an alkyl diphenyl ether oil, a multiple alkylate cyclopentane oil, and a silahydrocarbon oil may be incorporated in the lubricating oil composition of the present embodiment, as necessary, for the purpose of further improving the performance thereof or in order to impart further performance as long as the effect of the present invention is not impaired. Furthermore, various additives such as an antioxidant, an extreme pressure agent, a friction modifier, a metal deactivator, an antifoaming agent, a thickener, and a coloring agent may, as necessary, be blended singly or in combination of two or more thereof.

As the additive, an antioxidant commonly used in a lubricating oil can be used without particular limitation, and examples of the antioxidant include phenol-based compounds, amine-based compounds, phosphorus-based compounds, and sulfur-based compounds.

Examples of the extreme pressure agent include phosphorus-based compounds and sulfur-based compounds.

Examples of the friction modifier include molybdenum-based compounds such as molybdenum dithiocarbamate, and fatty acid derivatives such as glycerin monostearate.

Examples of the metal deactivator include benzotriazole-based, tolyltriazole-based, thiadiazole-based, and imidazole-based compounds.

Examples of the antifoaming agent include polyacrylates and styrene ester polymers.

Examples of the thickener include metal soaps (for example, lithium soap), silica, expanded graphite, polyurea, and clays (for example, hectorite or bentonite).

In the lubricating oil composition of the present embodiment, when the dinaphthyl ether compound is contained as a base oil, the content thereof is preferably approximately 50 to 100 mass % with respect to the entire (total mass) of the lubricating oil composition from the viewpoint of ensuring heat resistance. In this case, the content of the additives in the lubricating oil composition is preferably approximately 50 to 0 mass %.

Furthermore, it is also possible to use the dinaphthyl ether compound as an additive of a lubricating oil composition, and in this case, the content of the dinaphthyl ether compound is preferably approximately 1 to 49 mass % with respect to the entire (total mass) of the lubricating oil composition.

The present invention also includes a lubricating oil for high temperature and a heat-resistant grease each containing the dinaphthyl ether compound described above.

The lubricating oil composition, the lubricating oil for high temperature, and the heat-resistant grease described above are suitably used as a lubricant for bearings, a lubricant for impregnated bearings, a grease base oil, a freezer oil, a plasticizer, and the like. In particular, they can be suitably used as various lubricating oils to be used under high-temperature conditions, such as a bearing oil, a fluid bearing oil, an oil-containing bearing oil, a grease base oil, an oil-containing plastic oil, a gear oil, a jet engine oil, a heat insulating engine oil, a gas turbine oil, an automatic transmission oil, a vacuum pump oil, and a hydraulic operating fluid.

In addition, since the dinaphthyl ether compound described above is also superior in radiation resistance, it is conceivable that the naphthyl phenyl ether compound can be suitably used as a radiation-resistant lubricating oil or a radiation-resistant grease.

Although the present description discloses the techniques of various aspects as described above, the main technology among them is summarized below.

The dinaphthyl ether compound according to one aspect of the present invention is a compound represented by the following formula (1):

[Chemical Formula 3]

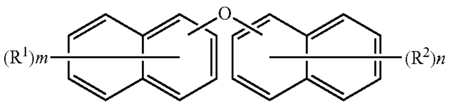

(1)

in the formula (1), $R^1$ and $R^2$ are the same or different and each represent a linear or branched hydrocarbon group having 6 to 32 carbon atoms; m and n are each a real number of 0 or more and satisfy $1.0 \leq m+n \leq 3.0$.

With such a configuration, it is possible to provide a compound having heat resistance superior to conventional lubricating oils.

The lubricating oil composition according to another aspect of the present invention is characterized by containing the dinaphthyl ether compound described above.

The lubricating oil for high temperature and the radiation-resistant lubricating oil according to still another aspect of the present invention are characterized by containing the dinaphthyl ether compound described above.

The heat-resistant grease and the radiation-resistant grease according to still another aspect of the present invention are characterized by containing the dinaphthyl ether compound described above.

The lubricating oil composition, the lubricating oil for high temperature, and the heat-resistant grease according to the present invention have excellent heat resistance, and thus are suitable for use under severe conditions (particularly, at high temperatures).

EXAMPLES

Hereinafter, examples of the present invention will be described, but the present invention is not limited thereto.

Synthesis of Compounds

Example 1: Compound 1

A four-necked flask equipped with a stirrer, a thermometer, a dropping funnel, and a cooling tube and having a capacity of 5 L was charged with 450 g (3.12 mol) of 2-naphthol, 862 g (6.24 mol) of potassium carbonate, 119 g (0.62 mol) of copper iodide, and 1000 g of NMP and purged with nitrogen, and then the temperature of the reaction system was heated to 175° C. When the temperature reached 120° C., dropwise addition of 1292 g (6.24 mol) of 1-bromonaphthalene was started. After completion of the dropwise addition, the mixture was stirred at 175° C. for 6 hours. After completion of the reaction, the mixture was allowed to spontaneously cool until the temperature reached 90° C. Then, 60 g of KYOWAAD 1000s (alkaline adsorbent; manufactured by Kyowa Chemical Industry Co., Ltd.) was added and the resulting mixture was stirred for 30 minutes. Subsequently, 40 g of activated clay was added, and the mixture was stirred at 90° C. for 30 minutes, and then a solid component was removed by filtration under reduced pressure. The filter cake was stirred in NMP and vacuum filtration was repeated three times. The obtained filtrate was distilled under reduced pressure at 80 Pa at 215° C. to 240° C. Thus, 1,2-dinaphthyl ether (dinaphthyl oxide: 1,2-DNO), which was solid at normal temperature, was obtained as a fraction. To the resulting mixture was added 5 weight % of active clay, and the resulting mixture was stirred at 90° C.

for 30 minutes, and contaminating grease and the like were removed by reduced pressure filtration. A GC chart of dinaphthyl ether is shown in FIG. 1 (the measurement conditions will be described later.). The purity was 94.0%. The dinaphthyl ether synthesized here was used also as a reaction material in Examples 2 to 6.

Next, a 500 mL four-necked flask equipped with a stirrer, a dropping funnel, and a thermometer was charged with 200 g (0.74 mol) of dinaphthyl ether and 2.33 g (0.017 mol) of anhydrous aluminum chloride, and the mixture was heated to 90° C. to dissolve the anhydrous aluminum chloride. Then, 83 g (0.37 mol) of 1-hexadecene was added dropwise over 2 hours while maintaining the temperature of the reaction system at 110° C., and a substitution reaction was performed. After completion of the dropwise addition, stirring was continued at 110° C. for 5 hours, and then the mixture was allowed to spontaneously cool until the temperature reached 90° C. Then, KYOWAAD 1000s in an amount 5.5 times the amount of anhydrous aluminum chloride was charged, and the mixture was stirred for 30 minutes. Subsequently, active clay in an amount 3.65 times the amount of anhydrous aluminum chloride was charged, the mixture was stirred at 90° C. for 30 minutes, and then anhydrous aluminum chloride and other acidic substances produced as by-products were removed by filtration under reduced pressure. The filtrate obtained here was distilled under reduced pressure at 320° C. at 80 Pa to remove unreacted raw materials and the like, thereby affording alkyl-substituted dinaphthyl ether (Compound 1: alkyl (C16)-1-(2-naphthyloxy)naphthalene (C16-1,2-DNO)) mainly composed of monoalkyl-substituted bodies. To the resulting mixture was added 5 weight % of active clay, and the resulting mixture was stirred at 90° C. for 30 minutes, and contaminating grease and the like were removed by reduced pressure filtration. The evaluation was performed for Compound 1 from which grease and the like had been removed. Hereinafter, in Examples 1 to 7 and Comparative Examples 1 to 4, grease and the like were removed, followed by the evaluation, in the same manner.

Example 2: Compound 2

An alkyl-substituted dinaphthyl ether (Compound 2: alkyl (C12)-1-(2-naphthyloxy)naphthalene (C12-1,2-DNO)) mainly composed of monoalkyl-substituted bodies was obtained under the same conditions as in Example 1 except that a four-necked flask having a capacity of 500 mL was used for the reaction, 120 g (0.44 mol) of the dinaphthyl ether obtained in Example 1, 1.05 g (0.0078 mol) of anhydrous aluminum chloride, and 37 g (0.22 mol) of 1-dodecene were used, and monoalkyl-substituted bodies were obtained as a fraction through distillation under reduced pressure at 260° C. to 300° C. at 80 Pa.

Example 3: Compound 3

An alkyl-substituted dinaphthyl ether (Compound 3: alkyl (C12)-1-(2-naphthyloxy)naphthalene (diC12-1,2-DNO)) mainly composed of dialkyl-substituted bodies was obtained under the same conditions as in Example 1 except that a four-necked flask having a capacity of 500 mL was used for the reaction, 100 g (0.37 mol) of the dinaphthyl ether obtained in Example 1, 1.57 g (0.012 mol) of anhydrous aluminum chloride, and 56 g (0.33 mol) of 1-dodecene were used, and unreacted raw materials, monoalkyl-substituted bodies and the like were removed by distillation under reduced pressure at 300° C. at 80 Pa.

Example 4: Compound 4

An alkyl-substituted dinaphthyl ether (Compound 4: branched alkyl (C20)-1-(2-naphthyloxy)naphthalene (bC20-1,2-DNO)) mainly composed of monoalkyl-substituted bodies was obtained under the same conditions as in Example 1 except that a four-necked flask having a capacity of 500 mL was used for the reaction, 135 g (0.50 mol) of the dinaphthyl ether obtained in Example 1, 2.46 g (0.019 mol) of anhydrous aluminum chloride, and 70 g (0.25 mol) of 2-octyl-1-dodecene were used.

Example 5: Compound 5

An alkyl-substituted dinaphthyl ether (Compound 5: branched alkyl (C24)-1-(2-naphthyloxy)naphthalene (bC24-1,2-DNO)) mainly composed of monoalkyl-substituted bodies was obtained under the same conditions as in Example 1 except that a four-necked flask having a capacity of 500 mL was used for the reaction, and 30 g (0.11 mol) of the dinaphthyl ether obtained in Example 1, 0.53 g (0.0040 mol) of anhydrous aluminum chloride, and 19 g (0.060 mol) of 2-decyl-1-tetradecene were used.

Example 6: Compound 6

An alkyl-substituted dinaphthyl ether (Compound 6: branched alkyl (C28)-1-(2-naphthyloxy)naphthalene (bC28-1,2-DNO)) mainly composed of monoalkyl-substituted bodies was obtained under the same conditions as in Example 1 except that a four-necked flask having a capacity of 500 mL was used for the reaction, 30 g (0.11 mol) of the dinaphthyl ether obtained in Example 1, 0.61 g (0.0046 mol) of anhydrous aluminum chloride, and 22 g (0.060 mol) of 2-dodecyl-1-hexadecene were used.

Example 7: Compound 11

A four-necked flask equipped with a stirrer, a thermometer, a dropping funnel, and a cooling tube and having a capacity of 2 L was charged with 120 g (0.83 mol) of 1-naphthol, 230 g (1.66 mol) of potassium carbonate, 32 g (0.17 mol) of copper iodide, and 300 g of NMP and purged with nitrogen, and then the temperature of the reaction system was heated to 175° C. When the temperature reached 120° C., dropwise addition of 345 g (1.66 mol) of 1-bromonaphthalene was started. After completion of the dropwise addition, the mixture was stirred at 175° C. for 6 hours. After completion of the reaction, the mixture was allowed to spontaneously cool to 90° C., 20 g of KYOWAAD 1000s was added, and the mixture was stirred for 30 minutes. Subsequently, 15 g of activated clay was added, and the mixture was stirred at 90° C. for 30 minutes, and then a solid component was removed by filtration under reduced pressure. The filter cake was stirred in NMP and vacuum filtration was repeated three times. The obtained filtrate was distilled under reduced pressure at 80 Pa at 215° C. to 240° C. Thus, 1,1-dinaphthyl ether (1,1-dinaphthyl oxide: 1,1-DNO), which was solid at normal temperature, was obtained as a fraction. To the resulting mixture was added 5 weight % of active clay, and the resulting mixture was stirred at 90° C. for 30 minutes, and contaminating grease and the like were removed by reduced pressure filtration. The purity was 99.6%.

Next, a 500 mL four-necked flask equipped with a stirrer, a dropping funnel, and a thermometer was charged with 77.7 g (0.29 mol) of dinaphthyl ether and 1.13 g (0.0085 mol) of anhydrous aluminum chloride, and the mixture was heated to 100° C. to dissolve the anhydrous aluminum chloride. Then, 32.3 g (014 mol) of 1-hexadecene was added dropwise over 2 hours while maintaining the temperature of the reaction system at 110° C., and a substitution reaction was performed. After completion of the dropwise addition, stirring was continued at 110° C. for 5 hours, and then the mixture was allowed to spontaneously cool until the temperature reached 90° C. Then, KYOWAAD 1000s in an amount 5.5 times the amount of anhydrous aluminum chloride was charged, and the mixture was stirred for 30 minutes. Subsequently, active clay in an amount 3.65 times the amount of anhydrous aluminum chloride was charged, the mixture was stirred at 90° C. for 30 minutes, and then anhydrous aluminum chloride and other acidic substances produced as by-products were removed by filtration under reduced pressure. The filtrate obtained here was distilled under reduced pressure at 320° C. at 80 Pa to remove unreacted raw materials and the like, thereby affording alkyl-substituted dinaphthyl ether (Compound 11: alkyl (C16)-1-(1-naphthyloxy)naphthalene (C16-1,1-DNO)) mainly composed of monoalkyl-substituted bodies. To the resulting mixture was added 5 weight % of active clay, and the resulting mixture was stirred at 90° C. for 30 minutes, and contaminating grease and the like were removed by reduced pressure filtration.

Comparative Example 1: Compound 7

A 500 mL four-necked flask equipped with a stirrer, a dropping funnel, and a thermometer was charged with 200 g (1.18 mol) of dinaphthyl ether and 1.00 g (0.0075 mol) of anhydrous aluminum chloride, and the mixture was heated to 90° C. to dissolve the anhydrous aluminum chloride. Then, 186 g (0.83 mol) of 1-hexadecene was added dropwise over 2 hours while maintaining the temperature of the reaction system at 100° C., and a substitution reaction was performed. After completion of the dropwise addition, stirring was continued at 100° C. for 1 hour, and then the mixture was allowed to spontaneously cool until the temperature reached 90° C. Then, KYOWAAD 1000s in an amount 5.5 times the amount of anhydrous aluminum chloride was charged, and the mixture was stirred for 30 minutes. Subsequently, active clay in an amount 3.65 times the amount of anhydrous aluminum chloride was charged, the mixture was stirred at 90° C. for 30 minutes, and then anhydrous aluminum chloride and other acidic substances produced as by-products were removed by filtration under reduced pressure. The filtrate (reaction filtrate A) obtained here was distilled under reduced pressure at 250° C. to 260° C. at 80 Pa, affording a monoalkyl-substituted alkyl diphenyl ether (Compound 7: alkyl (C16) diphenyl ether (C16-DPO)) as a fraction. To the resulting mixture was added 5 weight % of active clay, and the resulting mixture was stirred at 90° C. for 30 minutes, and contaminating grease and the like were removed by reduced pressure filtration.

Comparative Example 2: Compound 8

The reaction filtrate A obtained in Comparative Example 1 was distilled under reduced pressure at 290° C. at 80 Pa to remove unreacted raw materials, monoalkyl-substituted bodies and the like, thereby affording alkyl-substituted diphenyl ether (Compound 8: dialkyl (C16) diphenyl ether (diC16-DPO)) mainly composed of dialkyl-substituted bodies.

Comparative Example 3: Compound 9

A 500 mL four-necked flask equipped with a stirrer, a dropping funnel, and a thermometer was charged with 200 g (0.59 mol) of o-(m-phenoxyphenoxy)diphenyl and 0.72 g (0.0054 mol) of anhydrous aluminum chloride, and the mixture was heated to 90° C. to dissolve the anhydrous aluminum chloride. Then, 66 g (0.29 mol) of 1-hexadecene was added dropwise over 2 hours while maintaining the temperature of the reaction system at 100° C., and a substitution reaction was performed. After completion of the dropwise addition, stirring was continued at 100° C. for 1 hour, and then the mixture was allowed to spontaneously cool until the temperature reached 90° C. Then, KYOWAAD 1000s in an amount 5.5 times the amount of anhydrous aluminum chloride was charged, and the mixture was stirred for 30 minutes. Subsequently, active clay in an amount 3.65 times the amount of anhydrous aluminum chloride was charged, the mixture was stirred at 90° C. for 30 minutes, and then anhydrous aluminum chloride and other acidic substances produced as by-products were removed by filtration under reduced pressure. The filtrate obtained here was distilled under reduced pressure at 320° C. at 80 Pa to remove unreacted raw materials and the like, thereby affording Compound 9 (alkyl (C16)-2-(3-phenoxyphenoxy)diphenyl (C16-4P2E)) mainly composed of monoalkyl-substituted o-(m-phenoxyphenoxy)diphenyl. To the resulting mixture was added 5 weight % of active clay, and the resulting mixture was stirred at 90° C. for 30 minutes, and contaminating grease and the like were removed by reduced pressure filtration.

Comparative Example 4: Compound 10

Compound 10 (dialkyl (C16)-2-(3-phenoxyphenoxy)diphenyl (diC16-4P2E)) mainly composed of dialkyl-substituted o-(m-phenoxyphenoxy)diphenyl was obtained under the same conditions as in Comparative Example 3 except that a four-necked flask having a capacity of 500 mL was used for the reaction, 150 g (0.44 mol) of o-(m-phenoxyphenoxy)diphenyl, 1.85 g (0.014 mol) of anhydrous aluminum chloride, and 168 g (1.85 mol) of 1-hexadecene were used.

[$^1$H-NMR Measurement Conditions and Conditions for Calculation of Number of Substitution with Hydrocarbon Groups]

$^1$H-NMR was measured using a nuclear magnetic resonance apparatus JNM-ECX400 manufactured by JEOL Ltd. The measurement was conducted at a temperature of 80° C. with no use of solvents and standard substances.

The chemical shift was determined by performing measurement of the same compound using deuterated chloroform as a solvent and TMS as a standard substance and comparing the results. This is because peaks of deuterated chloroform and a benzene ring overlap each other, and an accurate integral value cannot be obtained.

Compounds 1 to 11 obtained were analyzed using $^1$H-NMR under the above conditions, and the mass average molecular weight of each compound was determined.

The number of substitution with hydrocarbon groups in Compounds 1 to 11 was determined through analyzing a $^1$H-NMR spectrum for each compound. Specifically, a calculation method will be described using the $^1$H-NMR spectrum of a model compound shown in FIG. 2.

Figure 2:
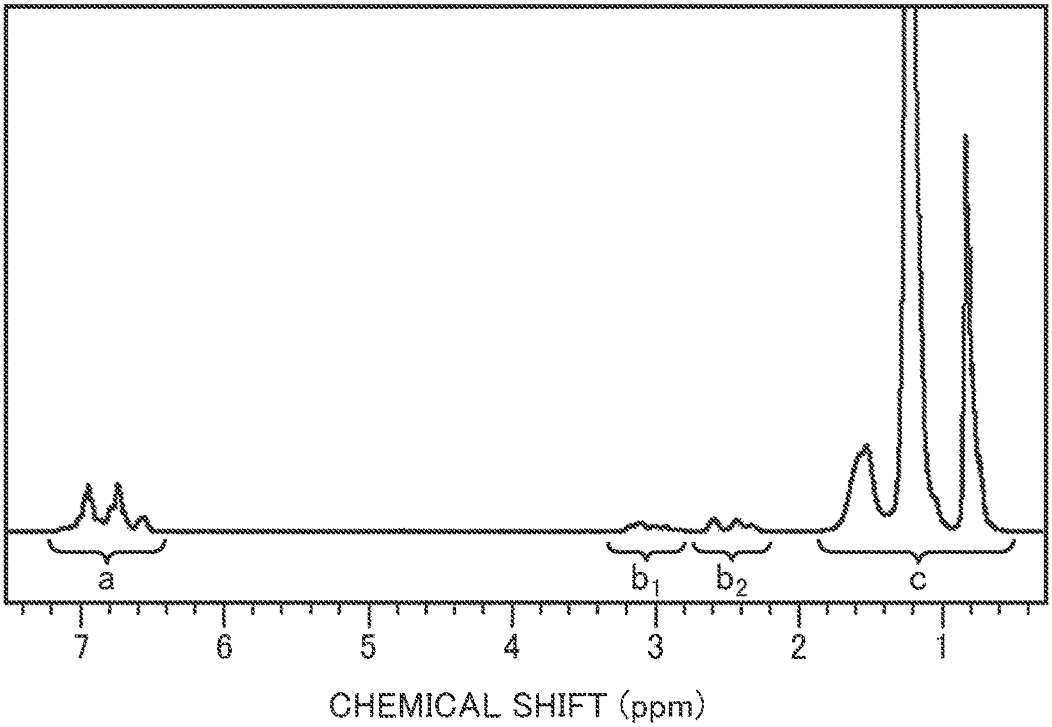
FIG. 2 shows a $^1$H-NMR spectrum of a model compound for determining the number of substitution with hydrocarbon groups.

In FIG. 2, a (chemical shift: 6.5 to 7.3) represents a peak of hydrogen of an aromatic ring. $b_1$ (chemical shift: 2.8 to 3.3) and $b_2$ (chemical shift: 2.2 to 2.7) represent peaks of hydrogen at the benzyl position. c (chemical shift: 0.5 to 1.9) represents a peak of hydrogen of a hydrocarbon group.

Based on the integrated values (ratios) of the peaks a, $b_1$, $b_2$, and c, the number of substitution with hydrocarbon groups is calculated by the following formula:

Number of substitution with hydrocarbon groups $(m+n)$=(number of hydrogen atoms of aromatic ring)$\times(b_1+b_2+c)$/[(average number of hydrogen atoms of hydrocarbon group)$\times a+b_1+b_2+c$]

<Purity Measurement>

[Gas Chromatography (GC) Measurement Conditions]

Gas chromatography was measured using GC-2010 Plus manufactured by Shimadzu Corporation. The column used was Ultra ALLOY+-17, and nitrogen gas was used as a carrier gas. The measurement temperature conditions were as follows: the temperature was held at 50° C. for 2 minutes, then raised 25° C. per minute up to 100° C., and from 100° C., raised 15° C. per minute up to 350° C., and held at 350° C. for 15 minutes.

<Evaluation Test>

[Measurement of Evaporation Amount by TG Method]

The evaporation amount determined by a TG method was measured using ST7200RV manufactured by Hitachi High-Technologies Corporation. Using air (200 ml/min) as a carrier gas and an aluminum deep pan as a sample container, an evaporation amount (%) of each compound at the time of holding 5 mg of a sample at a temperature of 250° C. for 30 minutes or 60 minutes was measured.

In this test, the evaluation criteria is that a compound satisfying an evaporation amount after 30 minutes of 10% or less and an evaporation amount after 60 minutes of 15% or less is determined to be acceptable.

[Thin film heating test]

0.5 g of each of the Compounds 1 to 11 was weighed in a 50 (I) concave dish made of material S45C. This was left at rest in a thermostatic chamber at 200° C., taken out from the thermostatic chamber every 2 hours, subjected to weight measurement, and checked for fluidity at the time of having been returned to room temperature. The time at which the fluidity at room temperature was lost was defined as a thin film life. In this test, a thin film life of 25 hours or more is determined to be acceptable.

[Lubricity Test (SRV)]

Lubricity was measured using SRV-5 manufactured by Optimol Instruments Priiftechnik GmbH. A ½ inch SUJ2 ball was used as an upper specimen, and a SK-5 plate was used as a lower specimen. After a running-in operation at a temperature of 40° C., a load of 50 N, and a speed of 40 mm/s for 50 seconds, this test at a temperature of 40° C., a load of 100 N, and a speed of 40 mm/s for 600 seconds was performed to measure a coefficient of friction (COF), and an average COF at 100 N was determined. In this test, an average COF of 0.150 or less is determined to be acceptable.

[Viscosity Properties]

The kinematic viscosity (mm$^2$/s) at 40° C. was measured and calculated in accordance with JIS K 2283 (2000).

The above results are summarized in Tables 1 and 2.

TABLE 1

| | Example 1 Compound 1 | Example 2 Compound 2 | Example 3 Compound 3 | Example 4 Compound 4 | Example 5 Compound 5 | Example 6 Compound 6 | Example 7 Compound 11 |
|---|---|---|---|---|---|---|---|
| Average number of substitution with hydrocarbon groups (n + m) | 1.23 | 1.17 | 2.21 | 1.22 | 1.40 | 1.28 | 1.32 |
| Number of carbon atoms of hydrocarbon group | 16 | 12 | 12 | 20 | 24 | 28 | 16 |
| Average molecular weight | 546 | 467 | 642 | 613 | 744 | 776 | 791 |
| [TG] Evaporation amount (%) at 250° C. for 30 minutes | 2.75 | 7.48 | 2.15 | 1.52 | 1.31 | 1.92 | 3.72 |
| [TG] Evaporation amount (%) at 250° C. for 60 minutes | 5.83 | 14.81 | 4.48 | 3.41 | 3.13 | 3.67 | 7.57 |
| Thin film life (hours) | 62 | 52 | 40 | 80 | 64 | 68 | 52 |
| Average COF at 100N | 0.103 | 0.111 | 0.106 | 0.109 | 0.104 | 0.094 | 0.103 |
| 40° C. Kinematic viscosity (mm$^2$/s) | 623.9 | 780.4 | 1648.5 | 1047.0 | 695.5 | 609.8 | 775.2 |

TABLE 2

| | Comparative Example 1 Compound 7 | Comparative Example 2 Compound 8 | Comparative Example 3 Compound 9 | Comparative Example 4 Compound 10 |
|---|---|---|---|---|
| Average number of substitution with hydrocarbon groups (n + m) | 1.05 | 2.22 | 1.32 | 1.77 |
| Number of carbon atoms of hydrocarbon group | 16 | 16 | 16 | 16 |
| Average molecular weight | 406 | 668 | 635 | 736 |
| [TG] Evaporation amount (%) at 250° C. for 30 minutes | 81.56 | 27.40 | 13.49 | 11.50 |
| [TG] Evaporation amount (%) at 250° C. for 60 minutes | 83.94 | 40.48 | 21.49 | 17.54 |
| Thin film life (hours) | 4 | 14 | 20 | 18 |
| Average COF at 100N | 0.162 | 0.187 | 0.114 | 0.110 |
| 40° C. Kinematic viscosity (mm$^2$/s) | 21.3 | 87.7 | 243.0 | 410.0 |

DISCUSSION

The results in Table 1 showed that the dinaphthyl ether compounds 1 to 6 and the compound 11 of Examples related to the present invention satisfied all the acceptance criteria for both the evaporation amount and the thin film life described above. It is known that the kinematic viscosity normally increases as the number of carbon atoms of a hydrocarbon group increases, but in the kinematic viscosity of the compound of the present invention decreased as the number of carbon atoms of a hydrocarbon group increases. In addition, the evaporation amount was controlled with the compounds of the present invention in Examples 2 and 3 as compared with Comparative Examples 2 and 3 even with an equivalent molecular weight. The evaporation amount was controlled in Examples 1 to 7 as compared with Comparative Examples 3 and 4 with the same number of six-membered ring structures. Furthermore, regarding the thin film life as a severer heat resistance evaluation, the heat resistance time in Examples 1 to 7 was twice or more as compared with Comparative Examples 3 and 4 with the same number of six-membered ring structures, and improvement in heat resistance was recognized. This is considered to be because the naphthalene structure prevents a polymerization reaction due to thermal oxidation.

On the other hand, according to the results shown in Table 2, the conventionally used diphenyl ether compounds of Comparative Examples 1 and 2 and the polyphenyl ether compounds of Comparative Examples 3 and 4 were large in the evaporation amount and short in thin film life, and could not obtain heat resistance as much as the compound of the present invention.

This application is based on Japanese Patent Application No. 2021-020368 filed on Feb. 12, 2021, the contents of which are included in the present application.

In order to embody the present invention, the present invention has been appropriately and sufficiently described through the embodiments with reference to the specific examples in the above, but it should be recognized that those skilled in the art can easily modify and/or improve the above-described embodiments. Therefore, as long as modifications or improvements carried out by a person skilled in the art do not depart from the scope of the claims described in the patent claims of the present invention, these modifications or improvements are interpreted as being encompassed by the scope of the claims.

INDUSTRIAL APPLICABILITY

Since the dinaphthyl ether compound of the present invention is excellent in heat resistance, it can be suitably used as a lubricating oil for high temperature, a heat-resistant grease, and the like, and has wide industrial applicability.

The invention claimed is:

1. A dinaphthyl ether compound represented by the following formula (1):

[Chemical Formula 1]

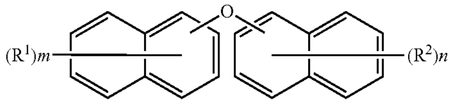

(1)

in the formula (1), $R^1$ and $R^2$ are the same or different and each represent a linear or branched hydrocarbon group having 6 to 32 carbon atoms; m and n are each a real number of 0 or more and satisfy $1.0 \leq m+n \leq 3.0$.

2. A lubricating oil composition comprising the compound according to claim 1.

3. A lubricating oil for high temperature comprising the compound according to claim 1.

4. A heat-resistant grease comprising the compound according to claim 1.

5. A radiation-resistant lubricating oil comprising the compound according to claim 1.

6. A radiation-resistant grease comprising the compound according to claim 1.

* * * * *